US011203615B2

(12) United States Patent
Nakamura (10) Patent No.: US 11,203,615 B2
(45) Date of Patent: Dec. 21, 2021

(54) CANCER TREATMENT DRUG (71) Applicant: NATIONAL UNIVERSITY CORPORATION HOKKAIDO UNIVERSITY, Hokkaido (JP)

(72) Inventor: Toru Nakamura, Sapporo (JP)

(73) Assignee: NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

(21) Appl. No.: 16/645,859

(22) PCT Filed: Sep. 10, 2018

(86) PCT No.: PCT/JP2018/033502
§ 371 (c)(1),
(2) Date: Mar. 10, 2020

(87) PCT Pub. No.: WO2019/050036
PCT Pub. Date: Mar. 14, 2019

(65) Prior Publication Data
US 2020/0270308 A1 Aug. 27, 2020

(30) Foreign Application Priority Data
Sep. 11, 2017 (JP) .............................. JP2017-174125

(51) Int. Cl.
| | |
|---|---|
| *A61K 35/76* | (2015.01) |
| *A61K 38/17* | (2006.01) |
| *A61K 38/00* | (2006.01) |
| *A61K 45/00* | (2006.01) |
| *A61K 48/00* | (2006.01) |
| *A61K 9/00* | (2006.01) |
| *A61P 1/18* | (2006.01) |
| *A61P 35/00* | (2006.01) |
| *A61P 43/00* | (2006.01) |
| *C07K 14/47* | (2006.01) |
| *C07K 7/08* | (2006.01) |
| *C07K 19/00* | (2006.01) |

(52) U.S. Cl.
CPC .............. *C07K 7/08* (2013.01); *A61P 35/00* (2018.01); *A61K 9/0019* (2013.01); *A61K 38/00* (2013.01)

(58) Field of Classification Search
CPC ........ A61K 35/76; A61K 38/00; A61K 38/17; A61K 45/00; A61K 48/00; A61K 9/0019; A61K 9/00; A61P 1/18; A61P 35/00; A61P 43/00; C07K 14/47; C07K 19/00; C07K 7/08
USPC ..... 530/300, 326, 327; 514/19.3, 21.3, 21.4, 514/21.5
See application file for complete search history.

(56) References Cited

U.S. PATENT DOCUMENTS

| | | |
|---|---|---|
| 7,601,826 B2 | 10/2009 | Nakamura et al. |
| 7,943,730 B2 | 5/2011 | Nakamura et al. |
| 2005/0026063 A1 | 11/2005 | Nakamura et al. |
| 2006/0270619 A1 | 11/2006 | Nakamura et al. |
| 2007/0253954 A1 | 11/2007 | Nakamura et al. |
| 2008/0063640 A1 | 3/2008 | Nakamura et al. |
| 2009/0162361 A1 | 6/2009 | Nakamura et al. |
| 2009/0215666 A1 | 8/2009 | Nakamura et al. |
| 2010/0093629 A1 | 4/2010 | Nakamura et al. |
| 2012/0028262 A1 | 2/2012 | Nakamura et al. |

FOREIGN PATENT DOCUMENTS

| | | |
|---|---|---|
| JP | 2006-500947 | 1/2006 |
| JP | 2009-502735 | 1/2009 |
| WO | 2016/187508 A2 | 11/2016 |

OTHER PUBLICATIONS

International Search Report dated Nov. 27, 2018 in corresponding International (PCT) Application No. PCT/JP2018/033502 with English-language translation.
International Preliminary Report on Patentability (Chapter I Patent Cooperation Treaty) dated Mar. 17, 2020 in corresponding International (PCT) Application No. PCT/JP2018/033502 with English-language translation.
Futaki et al., "Arginine-rich Peptides," The Journal of Biological Chemistry, 2001, vol. 276, No. 8, pp. 5836-5840.
Nakamura et al., "Overexpression of C16orf74 is involved in aggressive pancreatic cancers," Oncotarget, 2017, vol. 8, No. 31, pp. 50460-50475.
Tan et al., "Selective Inhibition of ErbB2-Overexpressing Breast Cancer In vivo by a Novel TAT-Based ErbB 2-Targeting Signal Transducers and Activators of Transcription 3-Blocking Peptide," Cancer Res., Apr. 1, 2006, vol. 66, No. 7, pp. 3764-3772.
Sato et al., "Molecular targeting of cell-permeable peptide inhibits pancreatic ductal adenocarcinoma cell proliferation," Oncotarget, 2017, vol. 8, No. 69, pp. 113662-113672.
Extended European Search Report dated May 3, 2021 in corresponding European Patent Application No. 18855070.1.

(Continued)

*Primary Examiner* — Julie Ha
(74) *Attorney, Agent, or Firm* — Wenderoth, Lind & Ponack, L.L.P.

(57) ABSTRACT

A peptide that includes a partial amino acid sequence of the C16orf74 protein, includes the cysteine at position 7 and/or the cysteine at position 14 of the C16orf74 protein, and inhibits dimer formation of the C16orf74 protein is provided. A pharmaceutical composition for cancer treatment that includes the peptide is also provided. A screening method for cancer treatment drugs that takes as the indicator inhibition of dimer formation of the C16orf74 protein is also provided.

13 Claims, 9 Drawing Sheets

Specification includes a Sequence Listing.

(56) References Cited

OTHER PUBLICATIONS

Database Geneseq [Online] Jan. 12, 2017, Fritsch Ef. et al., "Tumor-specific mutation containing human derived polypeptide SEQ ID:466", XP055796804, retrieved from EBI Database accession No. BDJ74287.
Kushibiki, Toshihiro et al., "Role of Dimerized C16orf74 in Aggressive Pancreatic Cancer: A Novel Therapeutic Target", Molecular Cancer Therapeutics, vol. 19, No. 1, Oct. 9, 2019, pp. 187-198, XP055797142.

CANCER TREATMENT DRUG

TECHNICAL FIELD

The present invention relates to a therapeutic drug for cancer and a screening method for a therapeutic drug for cancer.

BACKGROUND ART

Therapeutic outcomes for many cancers cannot yet be deemed high. For pancreatic cancer, for example, complete cure cannot be achieved with conventional chemotherapies, and even novel molecular target therapeutic drugs only provide a survival benefit of several weeks when being used in combination with a conventional chemotherapy; thus, development of a novel, promising therapeutic drug is an urgent task. The present inventors identified the novel gene, *Homo sapiens* chromosome 16 open reading frame 74 (C16orf74), which significantly contributes to the malignancy of pancreatic cancer, through comprehensive gene expression analysis using clinical specimens, and reported the usefulness thereof as a therapeutic target molecule for pancreatic cancer on the basis of protein expression and functional analysis (Non Patent Literature 1). Nevertheless, no novel therapeutic method targeting C16orf74 has been established.

CITATION LIST

Non Patent Literature

Non Patent Literature 1: Nakamura T, et al. Oncotarget. 2016 Jul. 28. [Epub ahead of print]

SUMMARY OF INVENTION

Problem to be Solved

Required is implementation of effective treatment for cancer. Specifically, it is required to find out a novel therapeutic drug targeting C16orf74. It is also required to find out a method for screening for a superior cancer treatment drug with ease.

Solution to Problem

The present inventors found that C16orf74 protein localizes immediately beneath cell membranes and forms a homodimer. The present inventors diligently studied for a dimer formation inhibitor with the idea that the function of C16orf74 can be inhibited to suppress cancer cell growth through inhibition of the dimer formation.

As a result, the present inventors have found that a peptide obtained by bonding a membrane-permeable peptide to the amino acid sequence of C16orf74 protein in the N terminus side inhibits the dimer formation of C16orf74 protein to effectively suppress the growth of cancer cells, leading to completion of the present invention.

Specifically, the present invention relates to the followings:

(1) a peptide including a partial amino acid sequence of C16orf74 protein, wherein the peptide includes one or both of cysteine corresponding to cysteine at position 7 of C16orf74 protein and cysteine corresponding to cysteine at position 14 of C16orf74 protein, and inhibits the dimer formation of C16orf74 protein;

(2) the peptide according to (1), including both of cysteine corresponding to cysteine at position 7 of C16orf74 protein and cysteine corresponding to cysteine at position 14 of C16orf74 protein;

(3) the peptide according to (2), being 12 to 20 amino acids in length;

(4) the peptide according to (3), including an amino acid sequence set forth in SEQ ID NO: 2;

(5) a mutant peptide of the peptide according to any one of (1) to (4), wherein the mutant peptide includes an amino acid sequence obtained by substituting, deleting, or adding one to several amino acids for a partial amino acid sequence of an amino acid sequence set forth in SEQ ID NO: 1, and inhibits the dimer formation of C16orf74 protein;

(6) the peptide according to any one of (1) to (5), wherein a membrane-permeable peptide is bonded to the peptide;

(7) a polynucleotide encoding the peptide according to any of (1) to (6);

(8) a vector including the polynucleotide according to (7);

(9) a pharmaceutical composition for cancer treatment, containing a substance that inhibits the dimer formation of C16orf74 protein;

(10) a pharmaceutical composition for cancer treatment, containing the peptide according to any of (1) to (6), the polynucleotide according to (7), or the vector according to (8);

(11) a pharmaceutical composition for cancer treatment, containing the peptide according to (6);

(12) the pharmaceutical composition for cancer treatment according to (11), to be intraperitoneally administered; and (13) a screening method for a cancer treatment drug, the method including the steps of:

(a) expressing a monomer of C16orf74 protein intracellularly to form a dimer in the presence and absence of a candidate agent;

(b) measuring the amount of the intracellular dimer formed; and then (c) determining that it is possible that the candidate agent is a drug for treatment of a cancer when the amount of the dimer formed in the presence of the candidate agent is reduced compared with the amount of the dimer formed in the absence of the candidate agent.

Advantageous Effects of Invention

Use of the cancer treatment drug of the present invention can dramatically improve therapeutic outcomes for cancer. If the screening of the present invention for a cancer treatment drug is used, superior cancer treatment drugs can be found with ease.

BRIEF DESCRIPTION OF DRAWINGS

FIGS. 3(*a*), 3(*b*), and 3(*c*) show graphs demonstrating inhibition of the dimer formation of C16oef74 protein by the peptide of the present invention in pancreatic cancer cells. The vertical axis in FIGS. 3(*a*), 3(*b*), and 3(*c*) shows relative amounts of dimer formation as that without addition of the peptide is assumed as 1.

DESCRIPTION OF EMBODIMENTS

The present invention relates to, in one aspect, a peptide including a partial amino acid sequence of the amino acid sequence of C16orf74 protein (SEQ ID NO: 1), wherein the peptide includes one or both of cysteine corresponding to cysteine at position 7 of C16orf74 protein and cysteine corresponding to cysteine at position 14 of C16orf74 protein (hereinafter, the peptide is occasionally abbreviated as "the peptide of the present invention"). However, the peptide of the present invention is not identical to the whole amino acid sequence of C16orf74 protein (SEQ ID NO: 1). Specific examples of the peptide of the present invention in this aspect include a peptide consisting of a partial amino acid sequence of C16orf74 protein, wherein the peptide includes one or both of cysteine corresponding to cysteine at position 7 of C16orf74 protein and cysteine corresponding to cysteine at position 14 of C16orf74 protein. Positions of amino acids in C16orf74 protein herein are designated as the position of the amino acid methionine at the N terminus is assumed as position 1. An amino acid in the peptide of the present invention is herein occasionally represented as "an amino acid corresponding to the amino acid at position x of C16orf74 protein". Unless otherwise specified, C16orf74 protein herein refers to a monomer of wild-type human C16orf74 protein.

The partial amino acid sequence of C16orf74 protein is a part of the amino acid sequence of C16orf74 protein set forth in SEQ ID NO: 1. The peptide of the present invention includes one or both of cysteine corresponding to cysteine at the 7th position from the N terminus (position 7) of C16orf74 protein and cysteine corresponding to cysteine at the 14th position from the N terminus (position 14) of C16orf74 protein. Preferably, the peptide of the present invention includes both of cysteine corresponding to cysteine at position 7 of C16orf74 protein and cysteine corresponding to cysteine at position 14 of C16orf74 protein. These cysteine residues are inferred to be involved in the dimer formation of C16orf74 protein. The peptide of the present invention inhibits the dimer formation of C16orf74 protein.

The length of the peptide of the present invention is not particularly limited, and is preferably 5 to 30 amino acids, more preferably 8 to 25 amino acids, and even more preferably 12 to 20 amino acids. Examples of such a preferable peptide of the present invention include a peptide including an amino acid sequence of C16orf74 protein from any amino acid at position 1, 2, 3, 4, or 5 to any amino acid at position 15, 16, 17, 18, 19, or 20. An example thereof includes, but is not limited to, a peptide including the amino acid sequence set forth in SEQ ID NO: 2.

The peptide of the present invention may be a mutant peptide. The mutant peptide of the present invention inhibits the dimer formation of C16orf74 protein. The mutant peptide of the peptide of the present invention includes a mutated amino acid sequence of wild-type C16orf74 protein, specifically, an amino acid sequence obtained by substituting, deleting, or adding one to several amino acids for a partial amino acid sequence of the amino acid sequence of wild-type C16orf74 protein (the amino acid sequence set forth in SEQ ID NO: 1). The term "several" means, for example, two, three, four, five, six, seven, eight, or nine. However, the mutant peptide of the peptide of the present invention retains a cysteine residue(s) corresponding to a cysteine residue(s) at position 7 and/or position 14 of wild-type C16orf74 protein. Specific examples of the mutant peptide of the present invention include a peptide consisting of a mutated amino acid sequence of wild-type C16orf74 protein.

In cases with amino acid substitution, conservative amino acid substitution is preferred. Examples of conservative amino acid substitution include the following: substitution among Phe, Trp, and Tyr for the case that an amino acid to be substituted is an aromatic amino acid; substitution among Leu, Ile, and Val for the case that an amino acid to be substituted is a hydrophobic amino acid; substitution between Gln and Asn for the case that an amino acid to be substituted is a polar amino acid; substitution among Lys, Arg, and His for the case that an amino acid to be substituted is a basic amino acid; substitution between Asp and Glu for the case that an amino acid to be substituted is an acidic amino acid; and substitution between Ser and Thr for the case that an amino acid to be substituted is an amino acid having a hydroxyl group.

The mutant peptide of the peptide of the present invention may be one including a non-natural amino acid, or one with any amino acid residue modified, or labeled one.

Those skilled in the art can produce the peptide of the present invention and a mutant peptide thereof by using chemical synthesis methods, gene engineering methods, and so on.

A membrane-permeable peptide may be bonded to the peptide of the present invention or a mutant peptide thereof. Such a peptide is efficiently transported to cancer cells, and can inhibit the dimer formation of C16orf74 protein in the cancer cells.

The membrane-permeable peptide may be any peptide that allows the peptide of the present invention to be transported into cancer cells. Membrane-permeable peptides are known. The membrane-permeable peptide to be bonded to the peptide of the present invention may be a known membrane-permeable peptide. A wide variety of membrane-permeable peptides are commercially available. Examples of membrane-permeable peptides include, but are not limited to, TAT peptide and peptides consisting of 8 to 11 arginine residues.

The membrane-permeable peptide may be bonded to any of the N terminus, C terminus, and inner amino acid residues of the peptide of the present invention or a mutant peptide thereof, but is preferably bonded to the N-terminal amino acid residue. The membrane-permeable peptide may be bonded directly or via a spacer to the N-terminal amino acid residue of the peptide of the present invention or a mutant peptide thereof. The spacer may be known one and may be, for example, a peptide consisting of several glycine residues.

Those skilled in the art can produce the peptide of the present invention or mutant peptide thereof to which a membrane-permeable peptide has been bonded by using known methods such as chemical synthesis methods and gene engineering methods.

The present invention relates to, in another aspect, a polynucleotide encoding the peptide of the present invention, a mutant peptide thereof, or a peptide obtained by bonding a membrane-permeable peptide to any of them. Methods for producing a polynucleotide are known, and those skilled in the art can produce the polynucleotide, for example, by using a chemical synthesis method.

The present invention relates to, in another aspect, a vector including the above polynucleotide. An expression vector including the above polynucleotide may be introduced into cancer cells to inhibit the dimer formation of C16orf74 protein in the cancer cells. A wide variety of vectors are known and even commercially available, and any of them can be appropriately selected for use.

As described above, the present inventors got the insight that the growth of cancer cells can be effectively suppressed by inhibiting the dimer formation of C16orf74 protein. The present invention relates to, in a further aspect, a pharmaceutical composition for cancer treatment containing a substance that inhibits the dimer formation of C16orf74 protein.

The type of cancer to be treated with the pharmaceutical composition for cancer treatment of the present invention is not limited as long as it expresses C16orf74. Examples of cancer to be treated with the pharmaceutical composition for cancer treatment of the present invention include pancreatic cancer, bladder cancer, neck cancer, and oral-and-lingual squamous cell cancer.

The substance that is contained in the pharmaceutical composition of the present invention and inhibits the dimer formation of C16orf74 protein is not particularly limited, and preferred examples include the peptide of the present invention, a mutant peptide thereof, a peptide obtained by bonding a membrane-permeable peptide to any of them, a polynucleotide encoding any of these peptides, and a vector including such a polynucleotide. The phrase "inhibit the dimer formation of C16orf74 protein" indicates inhibition of preferably 30% or more, more preferably of 50% or more, even more preferably of 60% or more, further preferably 70% or more of the dimer formation of C16orf74 protein.

The pharmaceutical composition of the present invention in a wide variety of dosage forms can be produced by using a known means or method. The pharmaceutical composition of the present invention is preferably a solution, and may be, for example, an injection or an infusion. More preferably, the pharmaceutical composition of the present invention is an injection.

The route of administration of the pharmaceutical composition of the present invention is not particularly limited, and the pharmaceutical composition of the present invention can be administered through a wide variety of routes. Preferably, the pharmaceutical composition of the present is intraperitoneally administered.

A particular example of the pharmaceutical composition of the present invention includes a pharmaceutical composition for cancer treatment containing the peptide of the present invention or mutant peptide thereof to which a membrane-permeable peptide has been bonded. Such a pharmaceutical composition can exert the effects when being intraperitoneally administered.

The dose of the pharmaceutical composition of the present invention may be an amount that suppresses the growth of cancer, or an amount that reduces or eliminates cancer. Physicians can determine such a dose in view of the condition of cancer in a patient, the body weight of the patient, and so on. In an example for intraperitoneal administration to adults, the pharmaceutical composition of the present invention may be given to a patient so that approximately 1 mg to several tens of mg/kg (body weight) of the peptide of the present invention is administered per day.

The pharmaceutical composition of the present invention may be used in combination with another anticancer agent and/or anticancer treatment.

The present invention provides, in a further aspect, a therapeutic method for cancer in a cancer patient, the method including administering a substance that inhibits the dimer formation of C16orf74 protein to the cancer patient.

The present invention provides, in a further aspect, use of a substance that inhibits the dimer formation of C16orf74 protein for production of a pharmaceutical composition for treating cancer.

The present invention provides, in a further aspect, a substance that inhibits the dimer formation of C16orf74 protein for use in treatment of cancer.

The present invention relates to, in still another aspect, a screening method for a cancer treatment drug, the method including the following steps of:

(a) expressing a monomer of C16orf74 protein intracellularly to form a dimer in the presence and absence of a candidate agent;

(b) measuring the amount of the intracellular dimer formed; and then (c) determining that it is possible that the candidate agent is a drug for treatment of a cancer when the amount of the dimer formed in the presence of the candidate agent is reduced compared with the amount of the dimer formed in the absence of the candidate agent.

The cells to be used in step (a) may be any cells that express the monomer of C16orf74 protein, and are preferably cancer cells. Many cancer cells are known, and any of them may be used. Alternatively, the cells may be ones obtained from a clinical sample of cancer. If cells with weak or no expression of C16orf74 protein are used, the monomer of C16orf74 protein may be forcedly expressed. Forced expression of C16orf74 protein can be carried out by incorporating a gene encoding it into an expression vector and introducing the vector into cells. Forced expression of the monomer of C16orf74 protein provides clearer screening results.

The candidate agent may be any type of substance. If the candidate agent is a peptide, a peptide to which a membrane-permeable peptide has been bonded may be used. If a membrane-permeable peptide is bonded to a peptide, the peptide is thereby transported into cells, and thus a step of injecting a candidate substance into cells can be omitted. If the candidate agent is a peptide, an expression vector incorporating a polynucleotide encoding the peptide may be used.

Through culturing cells in the presence and absence of a candidate agent, the dimer of C16orf74 protein can be intracellularly formed. Those skilled in the art can determine conditions for cell culture with ease in view of factors including the type of cells.

In step (b), the amount of the intracellular dimer formed of C16orf74 protein is measured. Measurement of the amount of the dimer formed can be performed through detection of the dimer of C16orf74 protein in a lysate of cultured cells. For example, the dimer of C16orf74 protein can be detected by using Native polyacrylamide gel electrophoresis.

In step (c), the amount of the dimer formed of C16orf74 protein in the presence of the candidate agent and the amount of the dimer formed of C16orf74 protein in the absence of the candidate agent are compared, and it is determined that it is possible that the candidate agent is a drug for treatment of a cancer when the amount of the dimer formed in the presence of the candidate agent is reduced compared with the amount of the dimer formed in the absence of the candidate agent. Reduction of the amount of the dimer formed is interpreted as inhibition of dimer formation. It may be determined that the candidate agent is probably a cancer treatment drug if the amount of the dimer formed is reduced, for example, by 50% or more, 60% or more, or 70% or more.

In the screening method of the present invention, a peptide that does not inhibit the dimer formation of C16orf74 protein (e.g., SEQ ID NO: 6) may be used as a negative control.

Each term in the present specification is intended to have a meaning commonly understood in the fields of medicine and biochemistry, unless otherwise stated. Representation of amino acid sequences is herein according to the one-letter coding or the three-letter coding, which are known.

Hereinafter, the present invention will be described in more detail and more specifically with reference to Examples; however, Examples do not limit the present invention.

EXAMPLE 1

(1) Verification of Dimer Formation of C16orf74 Protein

Figure 1:
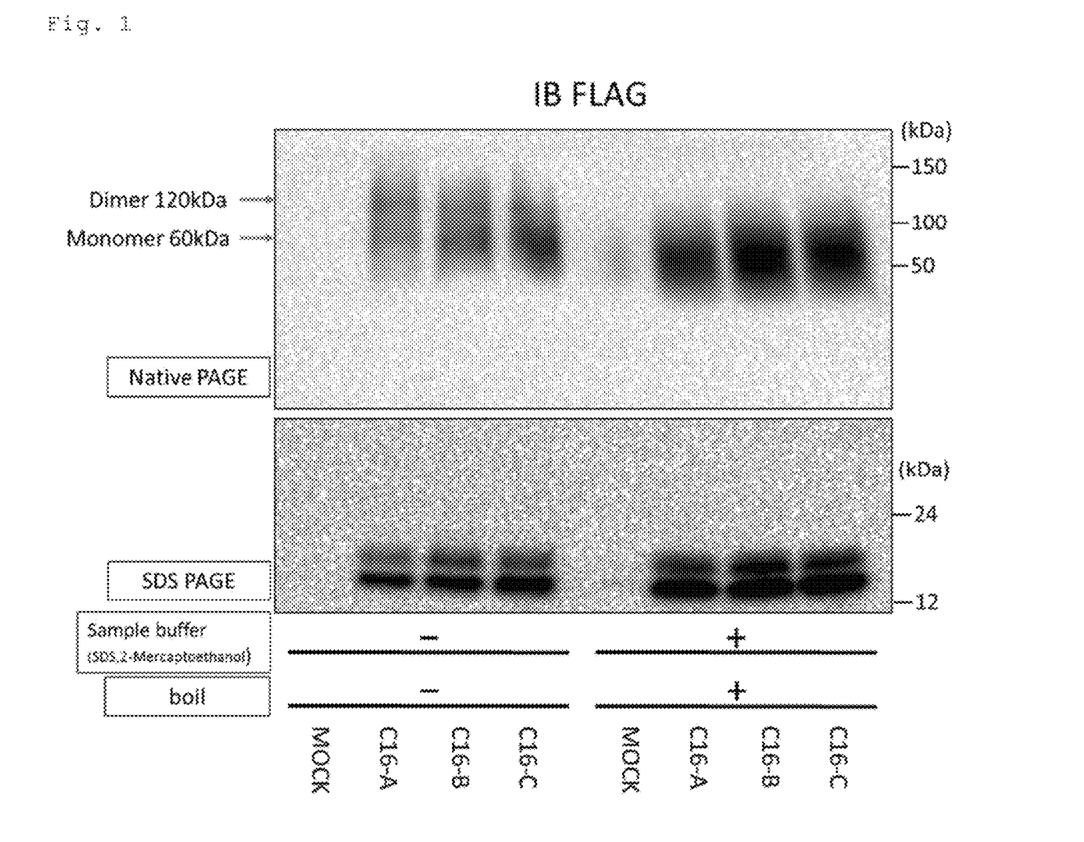
FIG. 1 shows immunoblotting demonstrating the dimer formation of C16oef74 protein. C16-A, C16-B, and C16-C represent three parallel experiment systems.

Pull-down assay was used for this verification. HEK293T cells were cotransfected with a vector to express a protein of Flag-tagged C16orf74 protein (pCAGGS-C16orf74-3×Flag) and a vector to express a protein of HA-tagged C16orf74 protein (pCAGGS-C16orf74-HA), and 24 hours thereafter a cell lysate was obtained and immunoprecipitation was carried out with agarose beads with an HA antibody attached thereto. The resulting immunoprecipitate was subjected to electrophoresis, and blotted with a Flag antibody. Experiment was conducted in three parallel systems. The results are shown in FIG. 1. In the figure, MOCK represents a case that empty vectors of pCAGGS were provided with a Flag tag and an HA tag and HEK293T cells were cotransfected therewith. A band of the Flag-tagged C16orf74 protein was found at an intended level (120 kDa). The results demonstrated that the Flag-tagged C16orf74 protein and the HA-tagged C16orf74 protein were directly bonding.

(2) Production of Peptide of Present Invention

An amino acid sequence from the N terminus to the 15th amino acid of C16orf74 protein, namely, MGLKMSCLKGFQMCV (SEQ ID NO: 2), and the polyarginine signal RRRRRRRRRRR (SEQ ID NO: 3) were bonded together via a GGG tag to afford the peptide RRRRRRRRRRR-GGG-MGLKMSCLKGFQMCV (SEQ ID NO: 4). In the same manner, the polyarginine signal RRRRRRRRR (SEQ ID NO: 5) was bonded to afford the peptide RRRRRRRRR-GGG-MGLKMSCLKGFQMCV (SEQ ID NO: 6).

Additionally a peptide designed to be incapable of bonding to C16orf74 protein was also synthesized. The peptide RRRRRRRRRRR-GGG-MGLKMSALKGFQMAV (SEQ ID NO: 7) is a peptide obtained by converting cysteine residues at the 7th and 14th positions from the N terminus in the amino acid sequence of SEQ ID NO: 2 into alanine residues. The peptide RRRRRRRRRRR-GGG-MGLK-MAAAKGFQAAA (SEQ ID NO: 8) is a peptide obtained by converting cysteine residues at the 7th and 14th positions from the N terminus and an upstream amino acid residue and downstream amino acid residue from each of the cysteine residues in the amino acid sequence of SEQ ID NO: 2 into alanine residues.

Figure 2:
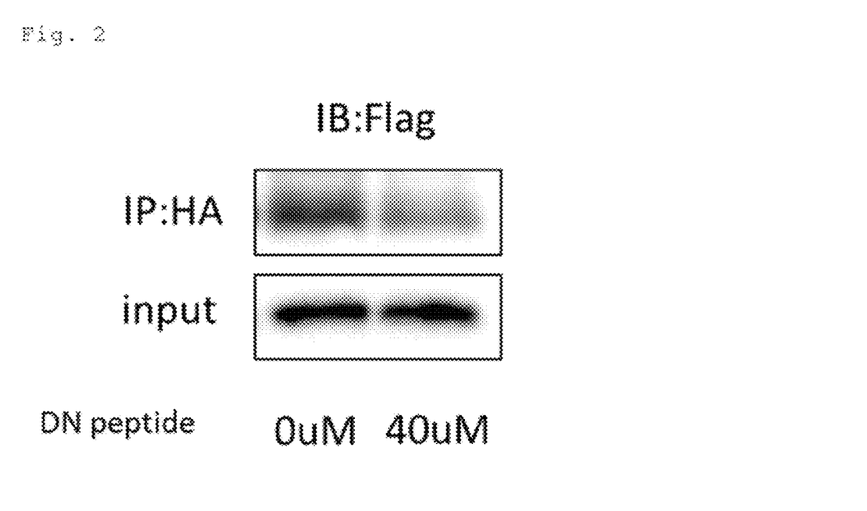
FIG. 2 shows immunoblotting demonstrating inhibition of the dimer formation of C16oef74 protein by the peptide of the present invention.

(3) Inhibition of Dimer Formation of C16orf74 Protein by Peptide of Present Invention HEK293T cells were transfected with pCAGGS-C16orf74-3×Flag and pCAGGS-C16orf74-HA, and cultured in the presence and absence of 40 μM of the peptide RRRRRRRRR-GGG-MGLKMSCLKGFQMCV (SEQ ID NO: 6) for 24 hours, and thereafter a band of the dimer was detected in the same manner as descried in (1). As shown in FIG. 2, the band was pale in the presence of 40 μM of the peptide (represented as DN-peptide in FIG. 2), which confirmed that the dimer formation was inhibited.

Figure 3A:
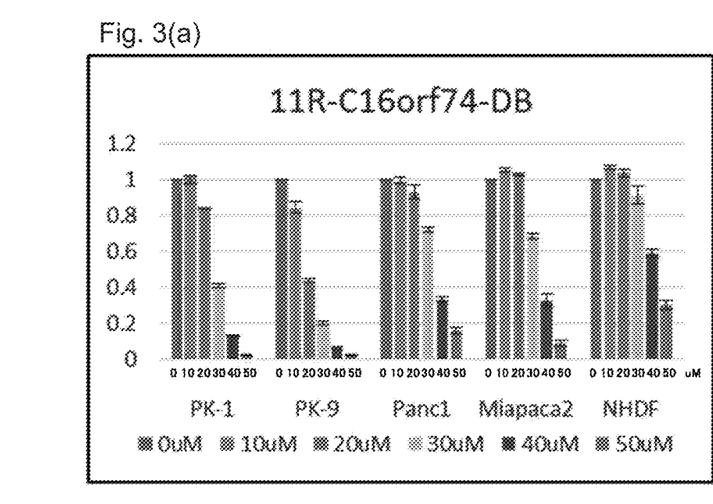
Figure 3B:
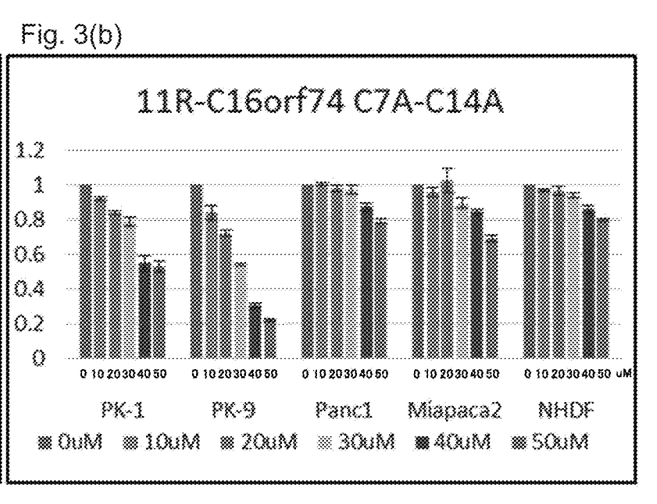
Figure 3C:
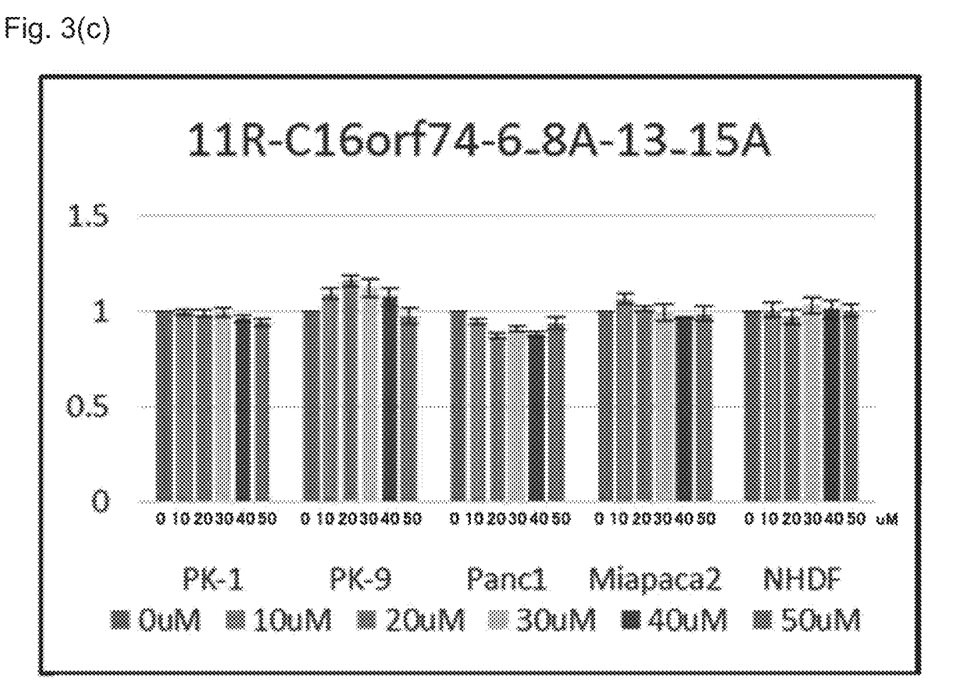

The same experiment as the above (3) was conducted by using the peptide RRRRRRRRRRR-GGG-MGLKMSCLKGFQMCV (SEQ ID NO: 4) (represented as 11R-C16orf74-DB in FIG. 3(a)), the peptide RRRRRRRRRRR-GGG-MGLKMSALKGFQMAV (SEQ ID NO: 7) (represented as 11R-C16orf74 C7A-C14A in FIG. 3(b)), and the peptide RRRRRRRRRRR-GGG-MGLK-MAAAKGFQAAA (SEQ ID NO: 8) (represented as 11R-C16orf74-6-8A-13-15A in FIG. 3(c)) with different concentrations to examine inhibition of the dimer formation of C16orf74 protein. For the cells, four types of human pancreatic cancer cells (PK-1, PK-9, Panc-1, Miapaca-2) and normal human dermal fibroblasts (NHDFs) were used. The results are shown in FIGS. 3(a), 3(b), and 3(c), which are 24 hour WST assays in which PK-1 and PK-9 (C16orf14 high expression) are compared to Panc1 and Miapaca2 (low expression). A p-value of p<0.05 was obtained at 30 μM.

In the four types of pancreatic cancer cells, 11R-C16orf74-DB inhibited the formation of the dimer of C16orf74 protein in a concentration-dependent manner. In PK-1 and PK-9, approximately 60% of the dimer formation was inhibited at a concentration of 30 μM. In Panc1 and Miapaca2, 60% or more of the dimer formation was inhibited at a concentration of 40 μM. In NHDFs, inhibition of the dimer formation weaker than in pancreatic cancer cells was found.

For 11R-C16orf74 C7A-C14A, inhibition of the dimer formation was found in PK-1 and PK-9, though the inhibition was weaker than in using 11R-C16orf74-DB. Almost no inhibition of the dimer formation was found in Panc1, Miapaca2, and NHDFs.

For 11R-C16orf74-6-8A-13-15A, no inhibition of the dimer formation was found in any of the cells.

Figure 4A:
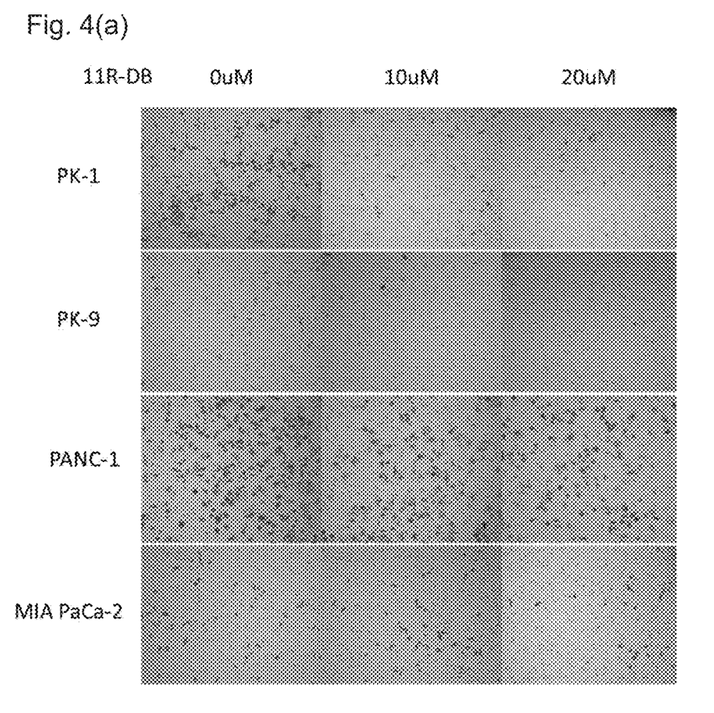
FIG. 4(a) shows photographs demonstrating suppression of the infiltration ability of pancreatic cancer cells by the peptide of the present invention.
Figure 4B:
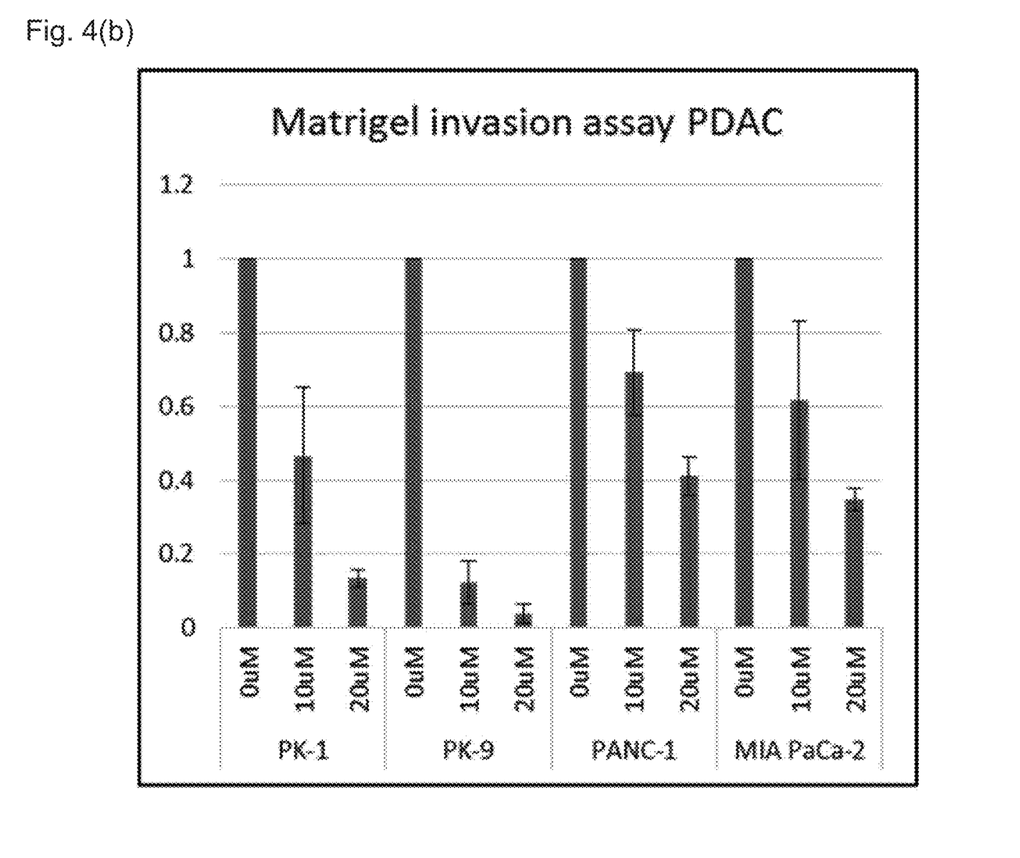
FIG. 4(b) shows a graph demonstrating suppression of the infiltration ability of pancreatic cancer cells by the peptide of the present invention. The vertical axis of the graph in FIG. 4(b) shows relative amounts of infiltration as that without addition of the peptide is assumed as 1.

(4) Suppression of Infiltration Ability of Pancreatic Cancer Cells by Peptide of Present Invention Examination was made with a Matrigel on the influence of the peptide of the present invention RRRRRRRRRRR-GGG-MGLKMSCLKGFQMCV (SEQ ID NO: 4) on infiltration ability of human pancreatic cancer cells (PK-1, PK-9, Panc-1, Miapaca-2). As shown in FIGS. 4(a) and 4(b), the peptide of the present invention inhibited infiltration of any of the cells in a concentration-dependent manner. FIGS. 4(a) and 4(b) compare PK-1 and PK-9 (C16orf14 high expression) to Panc1 and Miapaca2 (low expression). A p-value of $p<0.01$ was obtained at 20 μM.

Figure 5:
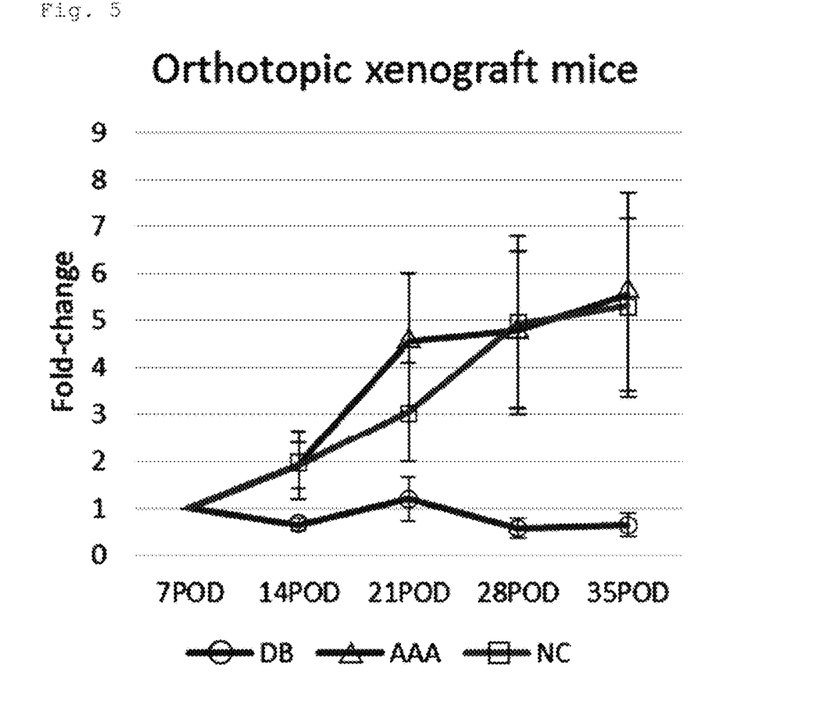
FIG. 5 shows a graph representing change over time (day 7, day 14, day 21, day 28, and day 35 after transplantation) in tumor fluorescence intensity in animals. The vertical axis shows fold-change of fluorescence intensity.
Figure 6:
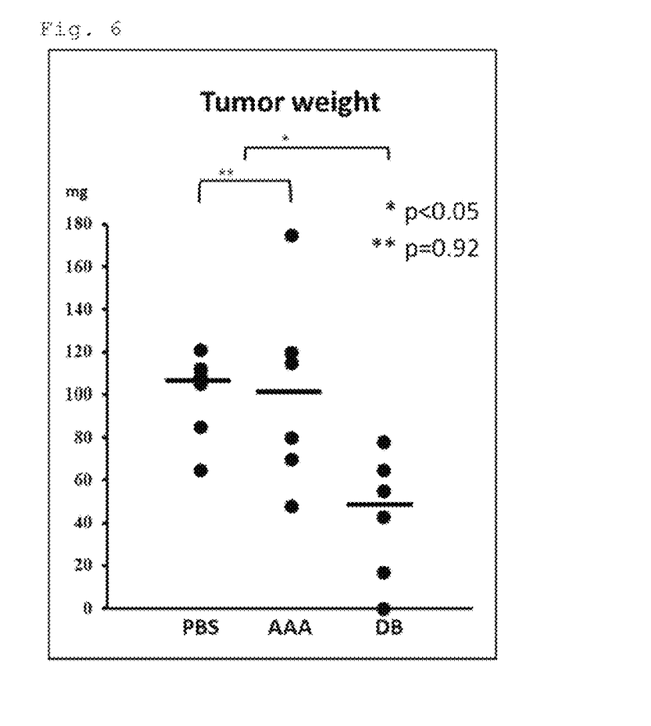
FIG. 6 shows a graph representing tumor weight in animals.

(5) Suppression of Tumor Growth by Peptide of Present Invention (5-1) Tumor Growth-Suppressing Effect of Peptide of Present Invention in Animals with Cancer Cells Transplanted on Back Thereof Human pancreatic cancer cells (PK-9) were transplanted to the back of each nude mouse (Balb/cA Jcl nu/nu mice, female, distributor: CLEA Japan, Inc.). The peptide of the present invention RRRRRRRRRRR-GGG-MGLKMSCLKGFQMCV (SEQ ID NO: 4), the peptide RRRRRRRRRRR-GGG-MGLKMAAAKGFQAAA (SEQ ID NO: 8), or PBS was intraperitoneally administered five times per week from day 7 to day 35 after the transplantation. During this period, body weight and tumor volume of the animals were measured, and fluorescence images were taken. On day 35 after the transplantation, tumor was resected, and the weight was measured. In terms of body weight of the animals, the group with administration of the peptide of the present invention exhibited a higher increasing tendency than the other administration groups. Change over time in tumor fluorescence intensity is shown in FIG. 5. The group with administration of the peptide of the present invention (represented as DB in FIG. 5) did not exhibit increase in fluorescence intensity, indicating that the tumor did not grow. The group with administration of the peptide of SEQ ID NO: 8 (represented as AAA in FIG. 5) and the PBS administration group (represented as NC in FIG. 5) exhibited increase in fluorescence intensity, indicating that the tumor grew. Tumor weight is shown in FIG. 6. The mean tumor weight was approximately 50 mg for the group with administration of the peptide of the present invention (represented as DB in FIG. 6), and, by contrast, approximately 100 mg to 110 mg for the other two groups. These results confirmed that the peptide of the present invention has strong tumor growth-suppressing effect in vivo.

Figure 7:
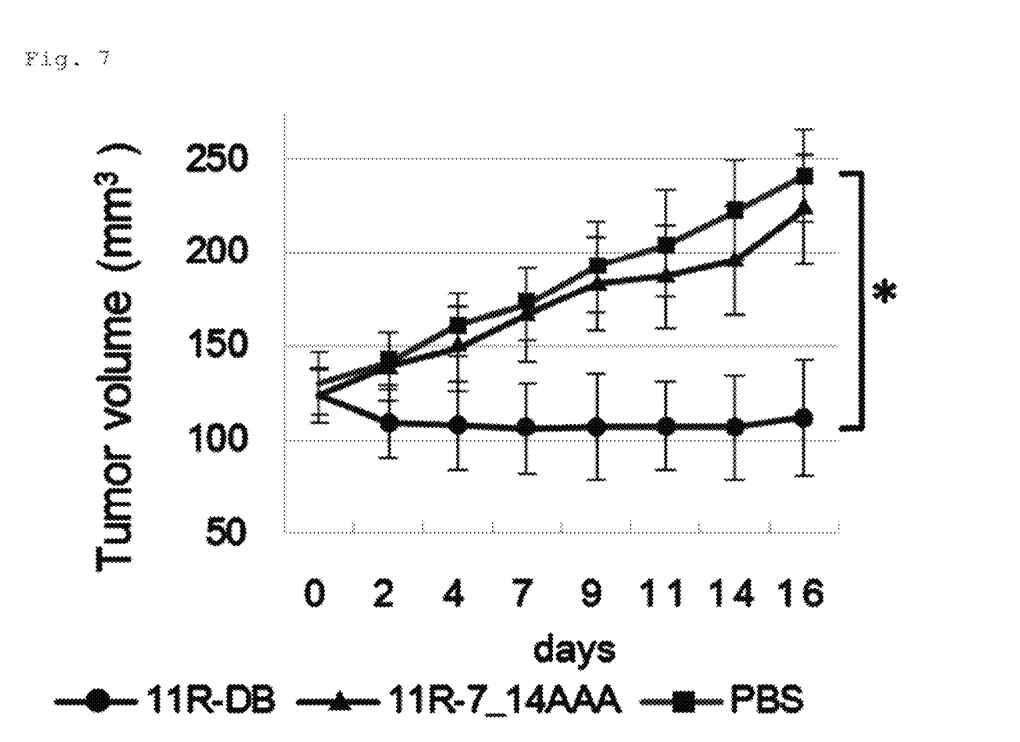
FIG. 7 shows a graph representing tumor volume in animals.
Figure 8:
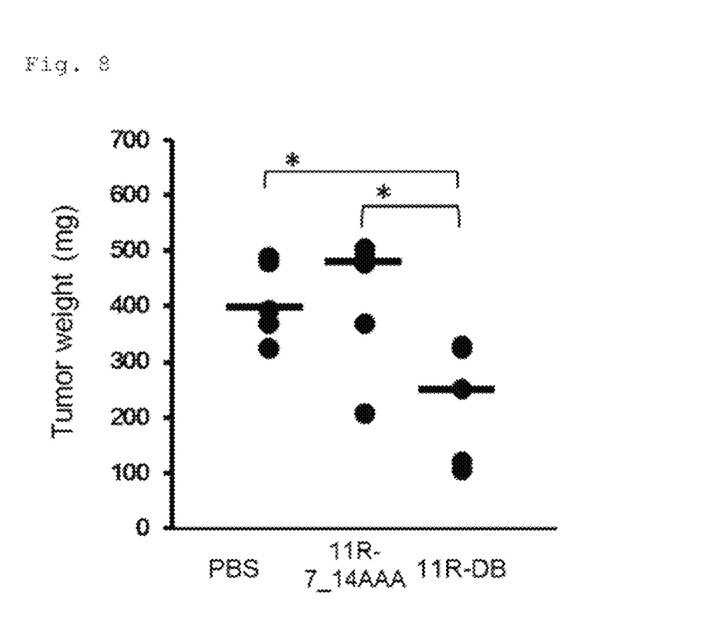
FIG. 8 shows a graph representing tumor weight in animals.

(5-2) Tumor Growth-Suppressing Effect of Peptide of Present Invention in Animals with Subcutaneously Injected Cancer Cells PK-9 cells were injected into the back of each nude mouse (Balb/cA Jcl nu/nu mice, female, distributor: CLEA Japan, Inc.). Two weeks after the injection, the peptide of the present invention RRRRRRRRRRR-GGG-MGLKMSCLKGFQMCV (SEQ ID NO: 4), the peptide RRRRRRRRRRR-GGG-MGLKMAAAKGFQAAA (SEQ ID NO: 8), or PBS was injected into the subcutaneous tissue in the vicinity of tumor five times per week (10 mg/kg/mouse). The administration period was 3 weeks. At the end of the administration period, tumor was resected and the tumor weight was measured. For the group with administration of the peptide of the present invention, the tumor volume decreased and then became constant (approximately 100 mm$^3$) (group 11R-DB in FIG. 7). For the group with administration of the peptide of SEQ ID NO: 8 and the group with administration of PBS, the tumor volume increased (group 11R-7_14AAA and group PBS in FIG. 7). The mean tumor weight of the group with administration of the peptide of the present invention (SEQ ID NO: 4) was approximately 250 mg (group 11R-DB in FIG. 8). For the group with administration of the peptide of SEQ ID NO: 8 and the group with administration of PBS (group 11R-7_14AAA and group PBS in FIG. 8), the tumor weight was also significantly larger than that for the group with administration of the peptide of the present invention (approximately 400 mg to 500 mg). These results confirmed that the peptide of the present invention has strong tumor growth-suppressing effect in vivo.

Figure 9:
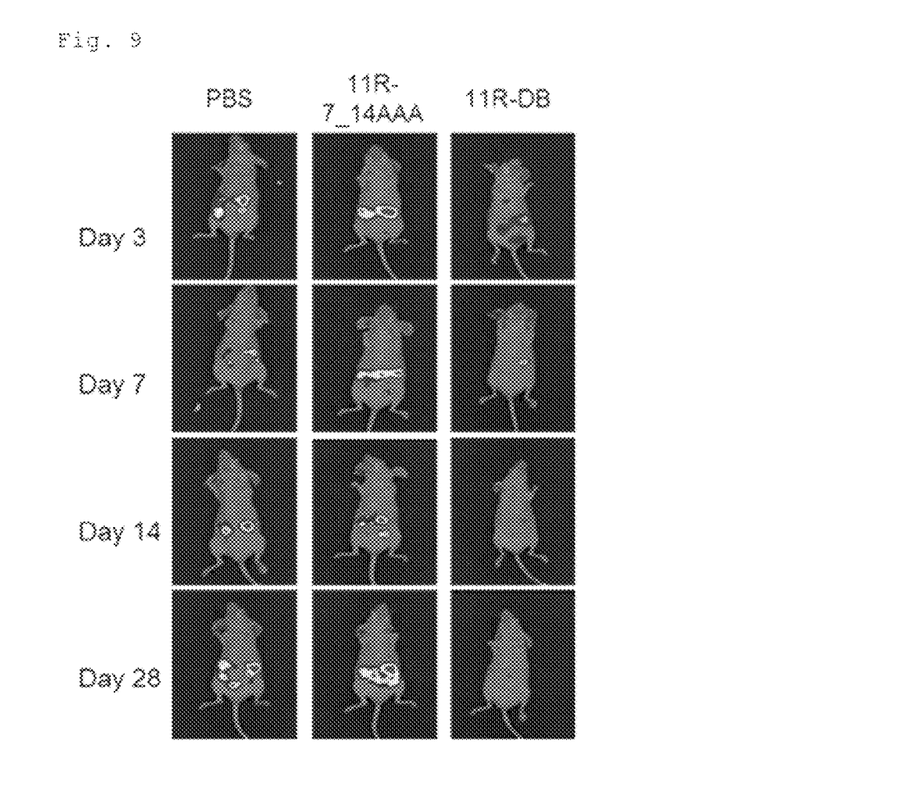
FIG. 9 shows change over time in fluorescence images of tumor in animals.
Figure 10:
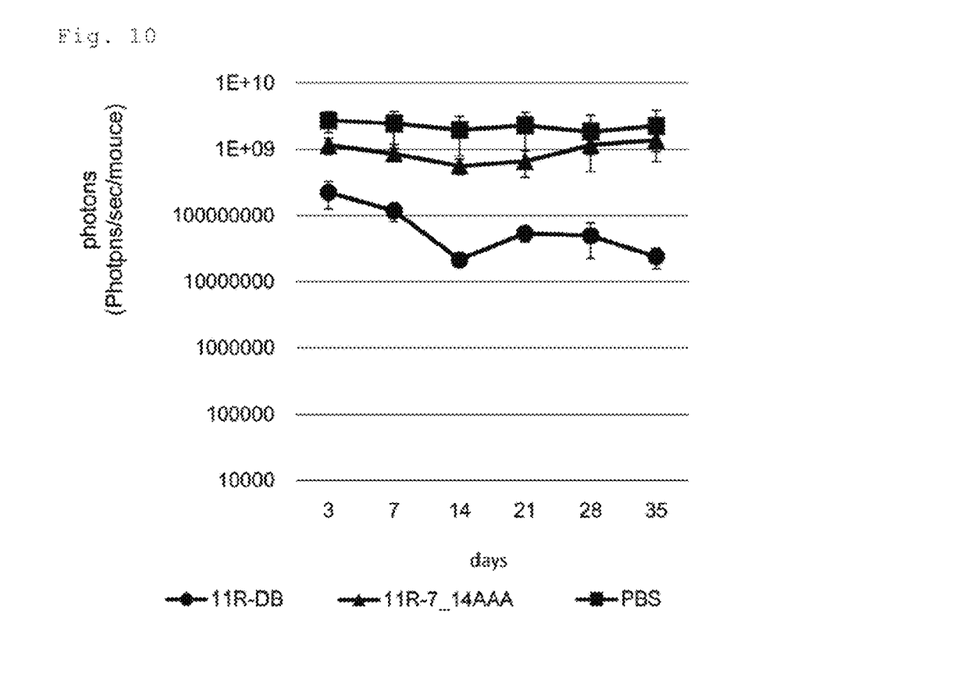
FIG. 10 shows a graph representing change over time in tumor fluorescence intensity in animals.
Figure 11:
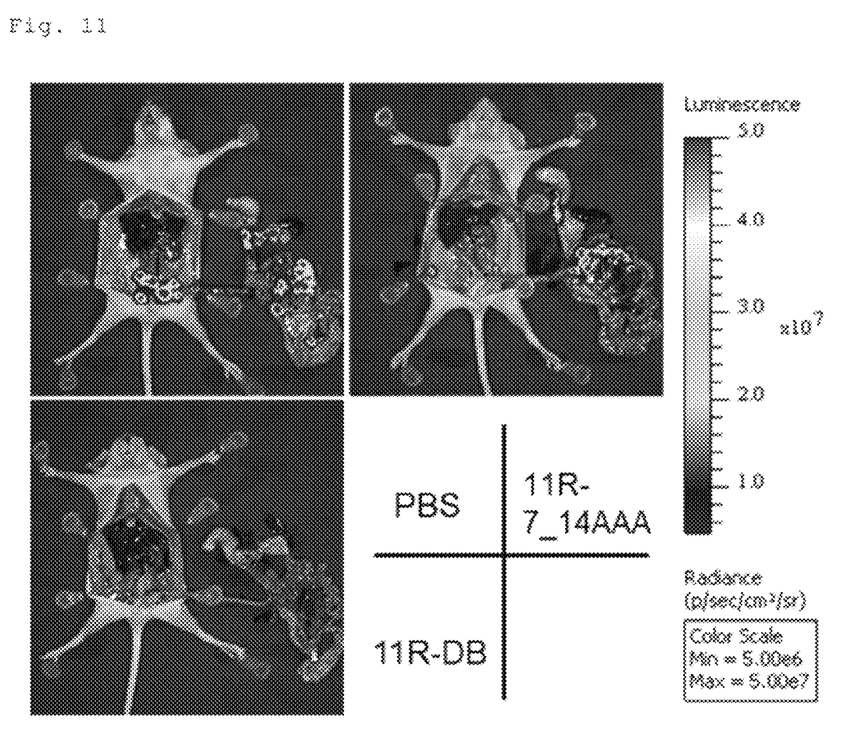
FIG. 11 shows fluorescence images of tumor in the peritoneum of animals.
Figure 12:
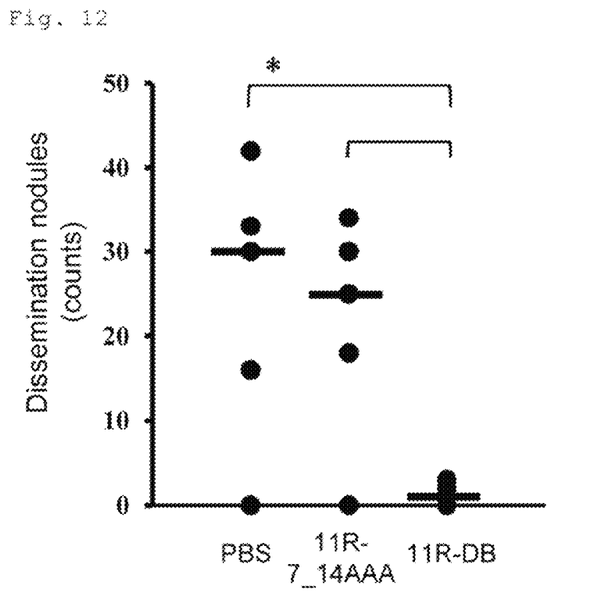
FIG. 12 shows a graph representing counts of dissemination nodules in animals.

(5-3) Tumor Survival- and Nodulation-Suppressing Effects of Peptide of Present Invention in Animals with Peritoneally Disseminated Cancer Cells PK-9 cells expressing luciferase (PK-9-td Tomato-luc2) were intraperitoneally injected into each nude mouse (Balb/cA Jcl nu/nu mice, female, distributor: CLEA Japan, Inc.). During a period from the day of the peritoneal dissemination to day 35, the peptide of the present invention RRRRRRRRRRR-GGG-MGLKMSCLKGFQMCV (SEQ ID NO: 4), the peptide RRRRRRRRRRR-GGG-MGLKMAAAKGFQAAA (SEQ ID NO: 8), or PBS was injected into the subcutaneous tissue in the vicinity of tumor five times per week (1 mg/kg/mouse). On days 3, 7, 14, 21, 28, and 35 after the peritoneal dissemination, tumor was imaged. The number of nodules was counted at the end of the peptide administration period. Administration of the peptide of the present invention suppressed the survival of tumor cells (group 11R-DB in FIG. 9 and FIG. 10). The survival of tumor cells was not suppressed in the group with administration of the peptide of SEQ ID NO: 8 and the group with administration of PBS (group 11R-7_14AAA and group PBS in FIG. 9 and FIG. 10). Administration of the peptide of the present invention largely reduced the number of nodules to one (group 11R-DB in FIG. 11 and FIG. 12). For the group with administration of the peptide of SEQ ID NO: 8 and the group with administration of PBS, the number of nodules did not reduce, and was 26 to 30 (group 11R-7_14AAA and group PBS in FIG. 11 and FIG. 12). These results confirmed that the peptide of the present invention has strong tumor growth-suppressing effect in vivo.

INDUSTRIAL APPLICABILITY

The pharmaceutical composition and screening method of the present invention are useful in the fields of cancer treatment medicaments, cancer research, and so on.

SEQUENCE LISTING FREE TEXT

SEQ ID NO: 1 represents the full-length amino acid sequence of C16orf74 protein.

SEQ ID NO: 2 represents an example of the amino acid sequence of the peptide of the present invention.

SEQ ID NO: 3 represents an example of the amino acid sequence of the polyarginate signal.

SEQ ID NO: 4 represents an example of the amino acid sequence of the peptide of the present invention with addition of a membrane-permeable peptide.

SEQ ID NO: 5 represents an example of the amino acid sequence of the polyarginate signal.

SEQ ID NO: 6 represents an example of the amino acid sequence of the peptide of the present invention with addition of a membrane-permeable peptide.

SEQ ID NO: 7 represents the amino acid sequence of a peptide obtained by converting cysteine residues at the 7th and 14th positions from the N terminus in the amino acid sequence of SEQ ID NO: 2 into alanine residues.

SEQ ID NO: 8 represents the amino acid sequence of a peptide obtained by converting cysteine residues at the 7th and 14th positions from the N terminus and an upstream amino acid residue and downstream amino acid residue from each of the cysteine residues in the amino acid sequence of SEQ ID NO: 2 into alanine residues.

The invention claimed is:

1. A peptide comprising a partial amino acid sequence of C16orf74 protein, wherein the peptide comprises both cysteine corresponding to cysteine at position 7 of C16orf74 protein and cysteine corresponding to cysteine at position 14 of C16orf74 protein, and inhibits dimer formation of C16orf74 protein, wherein the peptide is 12 to 20 amino acids in length.

2. The peptide according to claim 1, comprising an amino acid sequence set forth in SEQ ID NO: 2.

3. The peptide according to claim 1, wherein a membrane-permeable peptide is bonded to the peptide.

4. A pharmaceutical composition for cancer treatment, comprising the peptide according to claim 1.

5. A pharmaceutical composition for cancer treatment, comprising the peptide according to claim 3.

6. The pharmaceutical composition for cancer treatment according to claim 5, wherein the composition is for intraperitoneal administration.

7. A peptide comprising a partial amino acid sequence of C16orf74 protein, wherein the peptide comprises one or both of cysteine corresponding to cysteine at position 7 of C16orf74 protein and cysteine corresponding to cysteine at position 14 of C16orf74 protein, and inhibits dimer formation of C16orf74 protein, wherein the peptide is 12 to 20 amino acids in length.

8. The peptide according to claim 7, wherein a membrane-permeable peptide is bonded to the peptide.

9. A method for treating a cancer, comprising:
administering a therapeutically-effective amount of the peptide of claim 1 to a patient having the cancer, wherein the cancer is selected from the group consisting of pancreatic cancer, bladder cancer, neck cancer, and oral-and-lingual squamous cell cancer.

10. The method according to claim 9, wherein a membrane-permeable peptide is bonded to the peptide.

11. A method for treating a cancer, comprising:
administering a therapeutically-effective amount of the peptide of claim 7 to a patient having the cancer, wherein the cancer is selected from the group consisting of pancreatic cancer, bladder cancer, neck cancer, and oral-and-lingual squamous cell cancer.

12. The method according to claim 11, wherein a membrane-permeable peptide is bonded to the peptide.

13. A screening method for a cancer treatment drug, the method comprising the following steps of:

(a) expressing a monomer of C16orf74 protein intracellularly to form a dimer in the presence and absence of a candidate agent; and
(b) measuring the amount of the intracellular dimer formed;

wherein when the amount of the dimer formed in the presence of the candidate agent is reduced compared with the amount of the dimer formed in the absence of the candidate agent, the candidate agent is a drug for treatment of cancer.

* * * * *

SEQUENCE LISTING

<160> NUMBER OF SEQ ID NOS: 8

<210> SEQ ID NO 1
<211> LENGTH: 76
<212> TYPE: PRT
<213> ORGANISM: Homo sapiens

<400> SEQUENCE: 1

Met Gly Leu Lys Met Ser Cys Leu Lys Gly Phe Gln Met Cys Val Ser
1               5                   10                  15

Ser Ser Ser Ser Ser His Asp Glu Ala Pro Val Leu Asn Asp Lys His
            20                  25                  30

Leu Asp Val Pro Asp Ile Ile Ile Thr Pro Pro Thr Pro Thr Gly Met
        35                  40                  45

Met Leu Pro Arg Asp Leu Gly Ser Thr Val Trp Leu Asp Glu Thr Gly
    50                  55                  60

Ser Cys Pro Asp Asp Gly Glu Ile Asp Pro Glu Ala
65                  70                  75

<210> SEQ ID NO 2
<211> LENGTH: 15
<212> TYPE: PRT
<213> ORGANISM: Homo sapiens

<400> SEQUENCE: 2

Met Gly Leu Lys Met Ser Cys Leu Lys Gly Phe Gln Met Cys Val
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: leader sequence

<400> SEQUENCE: 3

Arg Arg Arg Arg Arg Arg Arg Arg Arg Arg Arg
1               5                   10

<210> SEQ ID NO 4
<211> LENGTH: 29
<212> TYPE: PRT
<213> ORGANISM: Artificial Sequence
<220> FEATURE:
<223> OTHER INFORMATION: fusion peptide

<400> SEQUENCE: 4

Arg Arg Arg Arg Arg Arg Arg Arg Arg Arg Arg Gly Gly Gly Met Gly
1               5                   10                  15

Leu Lys Met Ser Cys Leu Lys Gly Phe Gln Met Cys Val
            20                  25

<210> SEQ ID NO 5
<211> LENGTH: 9
<212> TYPE: PRT
<213> ORGANISM: Artificial Sequence
<220> FEATURE:
<223> OTHER INFORMATION: leader sequence

<400> SEQUENCE: 5

Arg Arg Arg Arg Arg Arg Arg Arg Arg
1               5

```
<210> SEQ ID NO 6
<211> LENGTH: 27
<212> TYPE: PRT
<213> ORGANISM: Artificial Sequence
<220> FEATURE:
<223> OTHER INFORMATION: fusion peptide

<400> SEQUENCE: 6

Arg Arg Arg Arg Arg Arg Arg Arg Arg Gly Gly Gly Met Gly Leu Lys
1               5                   10                  15

Met Ser Cys Leu Lys Gly Phe Gln Met Cys Val
            20                  25

<210> SEQ ID NO 7
<211> LENGTH: 29
<212> TYPE: PRT
<213> ORGANISM: Artificial Sequence
<220> FEATURE:
<223> OTHER INFORMATION: fusion peptide

<400> SEQUENCE: 7

Arg Arg Arg Arg Arg Arg Arg Arg Arg Arg Arg Gly Gly Gly Met Gly
1               5                   10                  15

Leu Lys Met Ser Ala Leu Lys Gly Phe Gln Met Ala Val
            20                  25

<210> SEQ ID NO 8
<211> LENGTH: 29
<212> TYPE: PRT
<213> ORGANISM: Artificial Sequence
<220> FEATURE:
<223> OTHER INFORMATION: fusion peptide

<400> SEQUENCE: 8

Arg Arg Arg Arg Arg Arg Arg Arg Arg Arg Arg Gly Gly Gly Met Gly
1               5                   10                  15

Leu Lys Met Ala Ala Ala Lys Gly Phe Gln Ala Ala Ala
            20                  25
```